United States Patent [19]

Winston et al.

[11] Patent Number: 5,645,853
[45] Date of Patent: Jul. 8, 1997

[54] CHEWING GUM COMPOSITIONS AND THE USE THEREOF FOR REMINERALIZATION OF LESIONS IN TEETH

[75] Inventors: Anthony E. Winston, East Brunswick; Norman Usen, Marlboro, both of N.J.

[73] Assignee: Enamelon Inc., East Brunswick, N.J.

[21] Appl. No.: 512,286

[22] Filed: Aug. 8, 1995

[51] Int. Cl.$^6$ ............................................. A61K 9/68
[52] U.S. Cl. ........................... 424/440; 424/48; 426/3
[58] Field of Search ........................ 424/48, 52, 57, 424/440; 514/782; 426/3

[56] References Cited

U.S. PATENT DOCUMENTS

| | | | |
|---|---|---|---|
| 2,605,229 | 7/1952 | Marcus | 252/317 |
| 3,679,360 | 7/1972 | Rubin | 423/308 |
| 3,913,229 | 10/1975 | Driskell et al. | 32/15 |
| 4,048,300 | 9/1977 | Tomlinson et al. | 424/52 |
| 4,080,440 | 3/1978 | Digiulio et al. | 424/49 |
| 4,083,955 | 4/1978 | Grabenstetter et al. | 424/49 |
| 4,097,935 | 7/1978 | Jarcho | 623/16 |
| 4,108,980 | 8/1978 | Duff | 424/52 |
| 4,150,112 | 4/1979 | Wagenknecht et al. | 424/48 |
| 4,159,315 | 6/1979 | Wagenknecht et al. | 424/48 |
| 4,177,258 | 12/1979 | Gaffar et al. | 424/52 |
| 4,183,915 | 1/1980 | Gaffar et al. | 424/52 |
| 4,233,288 | 11/1980 | Cornell | 424/48 |
| 4,265,877 | 5/1981 | Tenta | 424/48 |
| 4,348,381 | 9/1982 | Gaffar et al. | 424/52 |
| 4,397,837 | 8/1983 | Raaf et al. | 424/51 |
| 4,405,600 | 9/1983 | Besic | 424/57 |
| 4,515,770 | 5/1985 | Besic | 424/49 |
| 4,518,430 | 5/1985 | Brown et al. | 106/35 |
| 4,556,561 | 12/1985 | Brown et al. | 424/151 |
| 4,606,912 | 8/1986 | Rudy et al. | 424/52 |
| 4,610,873 | 9/1986 | Rudy et al. | 424/52 |
| 4,612,053 | 9/1986 | Brown et al. | 706/35 |
| 4,672,032 | 6/1987 | Slavkin et al. | 435/68 |
| 4,824,681 | 4/1989 | Schobel et al. | 424/48 |
| 5,037,639 | 8/1991 | Tung | 424/57 |
| 5,124,160 | 6/1992 | Zibell et al. | 424/48 |
| 5,139,769 | 8/1992 | Gaffar et al. | 424/57 |
| 5,268,167 | 12/1993 | Tung | 424/52 |
| 5,378,131 | 1/1995 | Greenberg | 424/48 |
| 5,427,768 | 6/1995 | Tung | 424/52 |
| 5,437,857 | 8/1995 | Tung | 424/52 |
| 5,460,803 | 10/1995 | Tung | 424/57 |

FOREIGN PATENT DOCUMENTS

WO94/18938  9/1994  WIPO .

*Primary Examiner*—Hoa Van Le
*Attorney, Agent, or Firm*—Depaoli & Frenkel, P.C.

[57] ABSTRACT

This invention relates to chewing gum compositions and methods utilizing same which are useful to remineralize subsurface dental enamel. More specifically, this invention relates to stable, single-part chewing gum compositions containing calcium and phosphate salts which when applied to lesions in dental enamel result in remineralization of subsurface dental enamel and/or mineralization of tubules in dentin thereby counteracting caries and/or hypersensitivity.

24 Claims, No Drawings

CHEWING GUM COMPOSITIONS AND THE USE THEREOF FOR REMINERALIZATION OF LESIONS IN TEETH

BACKGROUND OF THE INVENTION

1. Field of the Invention

This invention relates to chewing gum compositions and methods utilizing same which are useful to remineralize subsurface dental enamel. More specifically, this invention relates to stable, single-part chewing gum compositions containing calcium and phosphate salts which when applied to lesions in dental enamel result in remineralization of subsurface dental enamel and/or mineralization of tubules in dentin thereby counteracting caries and/or hypersensitivity.

2. The Prior Art

The primary component of the enamel and dentin in teeth is calcium phosphate in the form of calcium hydroxyapatite. This material highly insoluble at normal oral pHs. However, carious lesions form in teeth, when they are subjected to acids produced from the glycolysis of sugars by the action of various oral bacteria. This is because calcium phosphate salts are more soluble in acidic media.

Saliva is supersaturated with respect to calcium and phosphate ions. Saliva therefore helps protect teeth against demineralization and can slowly remineralize teeth which have become demineralized by acids. It is well known that the presence of fluoride ions can enhance the natural remineralization process and this is one of the accepted mechanisms by which fluoride toothpastes and rinses protect against caries. The efficacy of fluoride containing toothpastes and rinses to remineralize teeth is limited by the modest levels of calcium and phosphate in saliva. It is evident from the prior art that it is highly desirable to increase the available concentration of calcium and phosphate ions in the oral cavity to speed up the remineralization process. However, because of calcium phosphate's low solubility at the pH of saliva the addition of higher levels of dissolved calcium and phosphate ions is not easily accomplished.

Remineralization of dental enamel has been carried out experimentally both in vivo and in vitro. Some studies have concentrated on the remineralizing properties of saliva and synthetic solutions supersaturated with respect of hydroxyapatite. Such studies comprise the subject matter of U.S. Pat. Nos. 3,679,360 (Rubin) and 4,097,935 (Jarcho).

Generally, the supersaturated solutions or slurries used in these patents for remineralization experiments have been prepared from a single form of calcium phosphate. When a carious lesion is flooded with one of these supersaturated solutions, the calcium and phosphate ions in the form of precipitated hydroxyapatite remineralize the lesion.

However, these solutions are impractical for use for several reasons. First, the amount of calcium and phosphate ions available for remineralization in these supersaturated solutions is too low. It is reported that it takes approximately 10,000 unit volumes of the usual supersaturated solution to produce one unit volume of mineral. Thus, remineralization by this method requires both an excessive volume of fluid and an excessive number of applications. The supersaturated solutions are inherently limited in this respect because they cannot maintain their supersaturated state. When the hydroxyapatite precipitates out to the point where the solution is no longer supersaturated, new supersaturated solution must be introduced or the remineralization process stops.

Another problem with single calcium phosphate slurries is that as the hydroxyapatite precipitates out of solution, the pH of the solution changes. Unless the old solution is removed from contact with the tooth material, the solution may become too acidic or alkaline and damage the dental tissue.

U.S. Pat. Nos. 4,083,955 (Grabenstetter et al) and 4,397,837 (Raaf et al) provide processes utilizing various dentifrices, including chewing gums, for remineralizing demineralized enamel by the consecutive treatment of tooth surfaces with separate solutions containing calcium ions and phosphate ions. Fluoride ions may be present in the phosphate solutions. It is immaterial which ionic solution is used to treat the teeth first. By sequentially applying calcium and phosphate ions to the tooth surface high concentrations of the ions are able to diffuse or penetrate into lesions in solution form, where they precipitate as a calcium phosphate salt when ions from the second treatment solution diffuse in. While apparently successful this method involves the inconvenience of employing two different chewing portions, one containing the calcium ions and the other the phosphate ions. This method could be confusing because of the necessity of ensuring the proper sequence of gum portions and also inconvenient due to the plurality of sequential applications which can be found to be time consuming.

U.S. Pat. Nos. 5,037,639 and 5,268,167 (Tung) involve the use of amorphous calcium compounds such as: amorphous calcium phosphate (ACP), amorphous calcium phosphate fluoride (ACPF) and amorphous calcium carbonate phosphate (ACCP) for use in remineralizing teeth. These amorphous compounds or solutions which form the amorphous compounds when applied either onto or into dental tissue prevent and/or repair dental weaknesses such as dental caries, exposed roots and dentin sensitivity. The compounds are claimed to have high solubilities, fast formation rates and fast conversion rates (to apatite).

Remineralization is accomplished by bringing the amorphous compound into contact with the dental tissue. This can be done directly, i.e., putting an amorphous compound directly on the tooth, or indirectly through a carrier, i.e., incorporating the amorphous compound in a carrier such as a gel, a chewing gum, or a toothpaste and applying the carrier to the dental tissue. Once contact is established with the tooth, the amorphous calcium phosphate compounds will recrystalize to the less soluble apatite form in the lesion and reform the tooth. However, under conditions where amorphous calcium phosphate compounds are stable, the quantity of calcium and phosphate released is relatively low and, therefore, remineralization is slower than desirable.

International Patent WO 94/18938 (Greenberg) adds calcium glycerophosphate to a chewing gum. The calcium glycerophosphate is said to increase calcium and phosphate concentrations in plaque, increasing remineralization and decreasing demineralization. It may also inhibit large drops in pH in plaque and interfere with metabolism of S. mutans. A problem with this technology is that the glycerophosphate ion has to hydrolyze and release free phosphate ions before it can participate in the remineralization process. Hydrolysis occurs in the mouth due to the presence of phosphatase enzymes. However, the process is slow. The high concentration of calcium ions supplied by the calcium glycerophosphate therefore have time to dissipate before sufficient phosphate can be released to produce maximum remineralization.

Thus, the problem with known remineralization compositions and techniques is that there is not a one-part, stable remineralizing composition that may be suitably prepared as a chewing gum and the like which is not negatively affected by a rise in pH or temperatures or which can efficiently remineralize teeth.

There is a need for a method of remineralizing dental enamel which employs a stable, single-part remineralizing chewing gum composition which does not require excessive amounts of calcium and phosphate salts and inordinately long, frequent or sequential exposure times.

It is the object of the present invention to provide a single-part stable chewing gum composition and method for the remineralization and the prevention of demineralization of human teeth, which chewing gum composition and the use thereof are capable of effectively incorporating calcium ions, phosphate ions and, if desired, fluoride ions into the dental enamel, the chewing gum composition also being easily usable by the consumer and not differing significantly, in flavor and appearance, from customary chewing gums.

SUMMARY OF THE INVENTION

In accordance with the present invention the problems of remineralization, without demineralization are solved by applying to the teeth a stable, single-part chewing gum composition which contains remineralization components which do not react with one another until introduced into the oral cavity. The chewing gum contains at least one water-soluble calcium compound and at least one water-soluble inorganic phosphate compound and, optionally, at least one water-soluble fluorine compound. In this way the ions which effect remineralization can be absorbed by the dental enamel and their subsequent reaction causes rehardening of demineralized areas in the dental enamel.

It has been found that effective remineralizing treatments can be effected by providing stable, if desired non-aqueous, chewing gum, bubble gum, dragees, and similar preparations which are comprised of soluble salts containing high concentrations of calcium, phosphate and, if desired, fluoride ions and applying them to teeth at moderate pHs. However, the calcium ions must be prevented from reacting with the phosphate ions or fluoride ions until mastication begins and then preferably prevented from rapidly precipitating so as to allow ample time for diffusion of calcium and phosphate ions into the teeth.

In one embodiment of the invention, a stable, non-aqueous, single-part chewing gum is provided comprising at least one water-soluble calcium salt, at least one water-soluble phosphate salt, if desired at least one water-soluble fluoride compound yielding fluoride ions, and at least one other water-soluble, non-toxic divalent metal salt wherein the metal is other than calcium. The divalent metal is preferably a metal selected from the group consisting of magnesium, strontium, tin, and zinc and wherein, when the composition is contacted with water, the resulting solution has a pH of between about 4.0 and 7.0, preferably between about 5.0 and 5.75.

The stable, single-part remineralization system of this embodiment, in the form of a chewing gum, and the like, contains from about 0.01% to about 15.0% water-soluble calcium salt, greater than about 0.0002%, preferably from about 0.0002% to 1.0%, water-soluble, non-toxic divalent metal salt wherein the metal is other than calcium, from about 0.01% to 15.0% water-soluble phosphate salt, if desired from about 0.0001% to 0.5% fluoride releasing agent, and suitable pH adjusting compounds, i.e., acids, bases or buffers, such that the pH is between about 4.0 and 7.0, and preferably between about 5.0 and 5.75. Compositions are applied directly to the teeth when chewed and solubilized with saliva. It has been found that such combinations produce rapid remineralization of lesions and are much more effective than conventional fluoride containing dentifrices in remineralizing teeth.

The stable, single-part chewing gum may be prepared by adding to a gum base a dry-mix concentrated product which are mixed to make chewing gum products. The dry-mix product may be in the form of a powder, granular material, flake or the like. This embodiment contains from about 1.0% to 80.0% of the calcium salt and about 1.0% to 80.0% of the phosphate salt respectively. The chewing gum should contain about 0.005% to 20.0%, preferably about 0.1% to 7.0%, of the dry mix. Other adjuvants are, of course, included.

The compositions of the invention give substantially improved remineralization and prevention of demineralization of human teeth as compared with prior art compositions.

The disadvantages of the prior art methods are overcome by the present invention which effects subsurface remineralization rather than surface remineralization. Since dental caries begins as a subsurface demineralization of the dental enamel, subsurface remineralization arrests and repairs the carious lesion before any permanent structural damage to the tooth occurs. The present invention does not require preparation of the enamel surface, capping of the tooth, or removal of decay products. Further, the present invention may be conveniently practiced by the public without substantially changing their dental care habits.

DESCRIPTION OF THE INVENTION

The present invention lies in the discovery that a distinct improvement is realized when teeth are remineralized or desensitized by the use of chewing gums, i.e., chewing gum, bubble gum, dragees, and the like with contain soluble salts yielding ions which will react to form a desirable remineralizing or desensitizing precipitate. One preferred embodiment comprises the simultaneous use of a water-soluble salt of a divalent metal compound, other than calcium, which is admixed with the soluble salts which are placed in contact with the tooth surface. In this reaction selected cations and anions diffuse through the tooth surface to its demineralized subsurface. However, the additional divalent metal cations contained in the reactant solution with saliva stabilize the system from rapidly precipitating the calcium cations and the phosphate anions. The remineralizing cations and anions can then diffuse through the tooth surface to the demineralized subsurface without rapidly forming the precipitate which is bound to the tooth structure. As a result, the tooth's subsurface is more effectively remineralized or desensitized when an effective amount of the divalent metal cations is utilized.

As discussed above, the compositions of the invention are optionally non-aqueous. By "non-aqueous" is meant that the compositions do not include water in such an amount that it will adversely affect the stability required by the remineralization composition of the invention, i.e., the components of the compositions of the invention do not contain significant quantities of free water. However, they may contain salts with water of hydration. Preferably, the compositions of the invention include either no water or only traces of water.

By "effective amount of remineralizing system or agent" is meant an amount when used in accordance with this invention will bring about the remineralizing of teeth having carious lesions, or the mineralizing of normal teeth to prevent caries from forming and to inhibit hypersensitivity by utilizing a chewing gum having the various components in the amounts set forth below.

Concentrations of the cationic calcium and anionic phosphate soluble salts in the chewing gum are from about 0.01% to 15.0%. In accordance with the invention higher levels of salts are contemplated in order to maintain calcium and phosphate concentration in the mouth for long periods. Excess salt can be present, if desired. Concentrations from about 0.10% to 10.0% are preferred. The concentrations of the soluble salts containing the desired remineralizing anions are essentially the same as those for the water-soluble salts containing the desired cations.

Concentrations of the soluble, non-toxic divalent metal salts (other than calcium) in the chewing gum are greater than about 0.0002%, preferably between about 0.0002% to 1.0%, with concentrations of about 0.01% to 1.0% being most preferred.

Although many precipitates are within the broad scope of this invention, by depositing a precipitate less soluble than the original enamel, the remineralized subsurface can be made to be more resistant to demineralization than was the original enamel. If a fluoride ion is utilized, the remineralized enamel is more resistant to demineralization than was the original enamel. The concentration of salt containing fluoride ion in the chewing gum may be from about 0.0001% to 0.5%, but from about 0.0002% to 0.01% is preferred. High levels of fluoride are undesirable due to the potential for dental fluorosts and other toxic effects.

In order to effect remineralization of the dental enamel, an effective amount of the desired cations and anions must be employed In the oral cavity. The amount of solution generated in the mouth must contain at least 100 ppm of desired cations and 100 ppm of desired anions and preferably contains more than 1,000 ppm of desired cations and 1,000 ppm of desired anions. The solution must contain at least 10 ppm of divalent metal ions other than calcium, if employed, and, preferably contains more than 100 ppm thereof. If a fluoride compound is employed, it is desired to provide from the chewing gum a level of fluoride ions between about 1 ppm to 5,000 ppm, preferably between about 100 ppm to 500 ppm, in the oral cavity.

While the length of time of contact between the dissolved calcium and phosphate salts and the tooth's surface is not critical, it is necessary for the length of time to be great enough to allow diffusion of the ions through the tooth's surface to the demineralized subsurface. It is submitted that at least one minute of chewing is required for this diffusion and preferably it should be greater than fifteen minutes and even longer if possible. The desired extended time for such diffusion is a benefit acruing from the use of the divalent metal salts of this invention.

Upon mastication of the gum composition in the oral cavity with saliva, any resulting solution should have a pH of from about 4.0 to 7.0 and preferably between about 5.0 and 5.75 before and after the precipitation reaction, and be otherwise compatible in the oral environment. The ions must not combine prematurely in the solution to form a precipitate, but some must be able to diffuse through the surface of the tooth to a demineralized subsurface area and be able to form an insoluble salt with their counter ions.

The solutions in the oral cavity and the insoluble precipitates must have acceptable levels of toxicity (i.e., the particular ions, in the amounts used in the remineralization process, must be non-toxic).

In an embodiment of the invention the demineralizing composition is a stable, one-part dry-mix which can be subsequently mixed with a suitable gum base. Such dry-mix contains from about 1.0% to 80.0% of at least one calcium salt, from about 1.0% to 80.0% of at least one phosphate salt, from about 0.1% to 20.0% of at least one water-soluble divalent metal salt wherein the metal is other than calcium, and from 0 to about 1.0% of a fluoride salt. Suitable pH adjusting compounds, i.e., acids, bases, or buffers, are employed such that the resulting pH in use is between about 4.0 and 7.0, and preferably between 5.0 and 5.75.

The chewing gum should contain about 0.005% to 20.0%, preferably about 0.1% to 7.0%, of the dry mix. It is preferable to provide sufficient calcium and phosphate salt in the gum to ensure that the concentrations of each exceed about 100 ppm and preferably about 1000 ppm for an extended period.

In another preferred embodiment of the present invention, the remineralizing cationic phase of a chewing gum composition contains about 0.05% to 15.0%, preferably about 0.10% to 10%, of at least one soluble calcium salt yielding calcium ions and greater than about 0.0002%, preferably from 0.0002% to 1.0%, most preferably from about 0.01% to 1.0%, of at least one water-soluble divalent metal salt selected from the group consisting of magnesium, strontium, tin and zinc, with magnesium being preferred. The chewing gum also contains from about 0.01% to 15.0%, preferably about 0.10% to 10.0%, of dissolved phosphate salt yielding phosphate ions. From about 0.0001% to 0.5%, preferably from about 0.0002% to 0.01%, of a soluble fluoride salt yielding fluoride ions may be employed. Here too, suitable pH adjusting compounds are employed so that the resulting pH in use is between about 4.0 and 7.0, and preferably, between 5.0 and 5.75.

The resulting precipitate is a calcium phosphate or hydroxyapatite, the natural constituent of tooth enamel, with or without incorporated fluoride ions. Not only does this improved process result in remineralized enamel, but the remineralized enamel may be more resistant to subsequent demineralization than was the original enamel.

As the calcium compound it is, in principle, possible to employ any water-soluble toxicologically harmless calcium salt. A compound is considered to be water-soluble when at least 0.25 gram thereof dissolves in 100 ml of $H_2O$ at 20° C.

Suitable water-soluble calcium compounds are, for example, calcium chloride, calcium bromide, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, or mixtures of water-soluble calcium compounds. Calcium nitrate is preferred. In use, the compositions of the invention for the remineralization of human dental enamel should release to the saliva at least about 100 ppm and perferably at least about 1000 ppm of calcium ions to the saliva; the upper limit is about 35,000 ppm of calcium ions.

Suitable water-soluble inorganic phosphates within the scope of the present invention are, for example, alkali salts and ammonium salts of orthophosphoric acid, such as potassium, sodium or ammonium orthophosphate, monopotassium phosphate, dipotassium phosphate, tripotassium phosphate, monosodium phosphate, disodium phosphate and trisodium phosphate. In use, the concentration of the phosphate ions released to saliva should be at least about 100 ppm, and preferably at least about 1000 ppm to 40,000 ppm. Solubility in water is defined as in the case of the calcium compounds.

If desired, water-soluble salts yielding both calcium and phosphate ions, such as monobasic-calcium orthophosphate, may be employed.

As the stabilizing divalent metal compound it is also, in principle, possible to employ any water-soluble, non-toxic divalent metal compound which will stabilize the calcium and phosphate ions so that they do not rapidly or prematurely precipitate before diffusing into the teeth. In practice, however, it has been found that at least one member selected from the group consisting of magnesium, strontium, tin, and zinc, with magnesium being preferred, are the most effective in stabilizing the system.

Suitable magnesium compounds are, for example, magnesium acetate, magnesium ammonium sulfate, magnesium benzoate, magnesium bromide, magnesium borate, magnesium citrate, magnesium chloride, magnesium gluconate, magnesium glycerophosphate, magnesium hydroxide, magnesium iodide, magnesium oxide, magnesium propionate, magnesium D-lactate, magnesium DL-lactate, magnesium orthophosphate, magnesium phenolsulfonate, magnesium pyrophosphate, magnesium sulfate, magnesium nitrate, and magnesium tartrate. Preferred magnesium compounds are magnesium chloride, magnesium acetate and magnesium oxide.

Suitable strontium compounds are, for example, strontium acetate, strontium ammonium sulfate, strontium benzoate, strontium bromide, strontium borate, strontium caprylate, strontium carbonate, strontium citrate, strontium chloride, strontium gluconate, strontium glycerophosphate, strontium hydroxide, strontium iodide, strontium oxide, strontium propionate, strontium D-lactate, strontium DL-lactate, strontium pyrophosphate, strontium sulfate, strontium nitrate, and strontium tartrate. Preferred strontium compounds are strontium acetate, strontium chloride, strontium nitrate.

Suitable tin compounds are, for example, stannous acetate, stannous ammonium sulfate, stannous benzoate, stannous bromide, stannous borate, stannous carbonate, stannous citrate, stannous chloride, stannous gluconate, stannous glycerophosphate, stannous hydroxide, stannous iodide, stannous oxide, stannous propionate, stannous D-lactate, stannous DL-lactate, stannous orthophosphate, stannous pyrophosphate, stannous sulfate, stannous nitrate, and stannous tartrate. A preferred tin compound is stannous chloride.

Suitable zinc compounds are, for example, zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate. Preferred zinc compounds are zinc acetate, zinc chloride, zinc sulfate, and zinc nitrate.

The concentration of divalent metal ions is at least about 10 ppm, and preferably at least about 100 ppm, with about 20,000 ppm or more being the upper limit. Solubility in water is, again, as defined as in the case of calcium and phosphate compounds.

The compositions of the invention for the remineralization or prevention of demineralization of human teeth may also contain water-soluble fluoride compounds, the caries-prophylactic activity of which has for a long time been considered to be established. However, because of the potential for fluorosis or other toxic effects, the concentration of fluoride ion should preferably not exceed about 0.1%.

Suitable fluoride compounds are the alkali fluorides such as sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites.

Organic fluorides, such as the known amine fluorides are also suitable for use in the compositions of the invention.

Water-soluble alkali metal monofluorophosphates such as sodium monofluorophosphate, lithium monofluorophosphate and potassium monofluorophosphate, preferably, sodium monofluorophosphate may be employed. In addition other water-soluble monofluorophosphate salts may be employed including ammonium monofluorophosphate aluminum monofluorophosphate, and the like.

It has been found that even with the divalent metal salts used in the present invention some reaction between the calcium and phosphate ions still, in fact, may take place and cause some formation of insoluble calcium phosphate, etc. during storage. The present invention optionally overcomes this problem by including suitable stabilizing means or the like, either in addition to or instead of said divalent metal salts, which prevent reaction of the calcium ions with the phosphate ions and also with the fluoride ions if they are present.

Any orally acceptable material that stabilizes one or more of the calcium, phosphate and/or fluoride salts and prevents reaction of the salts with each other during storage of the chewing gum composition in a closed container or package can be employed in the present composition. Examples of suitable stabilizing agents or stabilizing means include desiccating agents, coating or encapsulating materials and mixtures of such stabilizing agents.

Examples of suitable desiccating agents include magnesium sulfate, sodium sulfate, calcium sulfate, calcium chloride and colloidal silica, e.g., colloidal silica particles sintered together in chainlike formations having surface areas of from about 50 to about 400 square meters per gram such as materials sold under the trademark Cab-O-Sil by Cabot Corp. It is believed that such materials act in stabilizing the compositions of the invention by, for example, absorbing any existing water either present in or contacted with the composition so as to prevent reaction of the calcium, phosphate and/or fluoride salts.

The stabilizing material is included in the composition of the invention in an amount effective so as to inhibit reaction between the calcium, phosphate and, if present, fluoride salts in the composition during storage in a closed container, but so as to allow release of sufficient calcium, phosphate and, if present, fluoride ions when the composition is contacted with saliva, i.e., during mastication of the chewing gum. Typically, the stabilizing material is included in the compositions of the present invention in an amount of up to about 7.5%, preferably from about 0.1% to 5%.

In an embodiment of this invention there is provided a stable single-part non-aqueous chewing gum for remineralizing dental enamel comprising: (i) from about 0.01% to 15.0%, preferably about 0.10% to 10.0%, water-soluble calcium salt; (ii) from about 0.01% to 15.0%, preferably about 0.10% to 10.0% water-soluble phosphate salt, optionally from about 0.0001% to 0.5% and preferably from about 0.0002% to 0.01% water-soluble fluoride salt, (iii) from about 0 to 7.5% of an orally acceptable dessicating agent; (iv) from about 10.0% to 95.0% of a gum base, and (v) wherein when the salts are contacted with saliva the pH is between about 4.0 and 7.0 and preferably between about 5.0 and 5.75.

Another method for inhibiting premature reaction of the calcium, phosphate and/or fluoride salts in the chewing gum compositions of the present invention is to provide a coating on or encapsulation thereof, e.g., with an oleophilic or, preferably, a polymeric material, which prevents reaction between the active materials. The presence of the coating on the various salts in the compositions of the present invention prevents reactions of the active material by other substances, for example, by traces of water in or absorbed into the system. Preferably, the coating is an edible coating. Suitable encapsulating or coating materials include oleophilic and other materials such as conventional edible gums, polymers which exhibit proportion ranging from hydrophilic to hydrophobic (water-insoluble), resins, waxes and mineral oils. The coating is preferably rinsable from the mouth.

In accordance with the invention a polymer employed for coating the water-soluble calcium and/or phosphate salt particles and the like of the invention is selected from hydrophilic organic polymers and hydrophobic (water-insoluble) organic polymers and mixtures thereof.

A hydrophilic polymer employed for coating the remineralizing salt particles is selected from water-soluble and water-dispersible organic polymers. A mixture of polymers can be employed, and a content of between about 5.0% to 95.0% of a water-insoluble polymer, based on the coating weight, can be included with a hydrophilic polymer.

The term "hydrophilic" as employed herein refers to an organic polymer which has a water-solubility of at least about one gram per 100 grams of water at 25° C. The term "hydrophobic" or "water-insoluble" as employed herein refers to an organic polymer which has a water solubility of less than about one gram per 100 grams of water at 25° C.

Suitable hydrophilic polymers for coating remineralizing salt particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, and the like. Polyvinyl acetate is illustrative of a water-insoluble polymer which can be included as an additional coating component to moderate the hydrophilicity of a hydrophilic polymer coating.

Suitable water-insoluble polymers, alone or in combination with one or more other components, for coating remineralizing salt particles include polyvinyl acetate, polyacrylamide, polyvinyl chloride, polystyrene, polyethylene, polyurethane, and the like.

The application of the polymer coating to the blend of calcium, phosphate, and other salt particles of the invention process is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethylformamide, and the like, as appropriate for a selected polymer species. A coating polymer also can be applied in the form of an emulsion or suspension. After the coating medium is applied to the particles, the solvent medium is removed by evaporation, thereby forming a continuous film coating which encapsulates the discrete crystallite particles.

The coating thickness on the surface of the salt typically will vary in the range between about 0.1–20 microns. The coating can consist of a single layer or multiple layers. The polymeric coating can constitute between about 5.0% to 50.0% of the total dry weight of the coated particles.

For purposes of release of the core matrix remineralizing calcium phosphate and, if desired, fluoride salts in the encapsulated particles when introduced into the aqueous environment, a surface coating of water-insoluble polymer of the oral cavity may have a content between about 5.0% to 30.0% weight percent of a particulate water-extractable organic or inorganic filler, such as sodium monosaccharide or disaccharide, sorbitol powder, mannitol, and the like.

The rate of release of remineralizing salt core matrix content of the encapsulated particles under aqueous conditions can be controlled by the quantity and type of polymer coating on the particle surface.

Low molecular weight hydrophilic polymers will release the particle core matrix content at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release the particle core matrix content at a relatively fast rate. Polyethylene oxide (M.W. of 4,000,000) or partially hydrolyzed polyvinyl acetate will release at a relatively slow rate. Polyvinylpyrrolidone will release the particle core matrix content at an immediate rate, when the encapsulated particles incorporated into a chewing gum is masticated in the mouth.

A present invention encapsulated remineralizing salt particle composition exhibits a unique combination of properties because of the novel physical form of the free-flowing, but substantially inert, polymer-coated particles when utilized as an ingredient in chewing gums.

Examples of suitable oleophilic coatings or enscapsulating materials include paraffin, mineral oil, edible oils such as peanut oil, coconut oil, palm oil, or safflower oil, oleophilic organic esters such as isopropyl siloxane myristate or isopropyl palmitate, edible polysiloxanes, and the like.

Encapsulating salts with a mixture of paraffin and waxes is also suitable.

By employing mineral oil as an oleophilic coating material for the calcium, phosphate and/or fluoride salts in the compositions of the invention, one other advantageous characteristic is provided. Specifically, oral bacteria known to be adversely affected by oleophilic materials. Thus, the mineral oil used in the compositions of the invention will help in removing undesired bacteria during the course of treatment.

The coating should be of a thickness and composition so that it either readily dissolves, disperses or emulsifies in water, e.g., in the mouth during chewing, or disintegrates during such action to release the active materials, i.e., one or more salts.

If the oleophilic material used for the coating is water insoluble, such as mineral oil, the coating phase can be pre-emulsified with a non-ionic, non-aqueous surfactant such as a hydrophilic ethoxylated sorbitan monooleate, e.g., the material sold under the trademark Tween. In this manner, when the composition is placed in water, the mineral oil or other olephilic coating on the particles is emulsified more readily than without the emulsification agent being present. Other similar surfactants can be employed such as sodium lauryl sulfate and other non-ionic surfactants.

In an embodiment of this invention there is provided a stable single-part non-aqueous chewing gum for remineralizing dental enamel comprising: (i) from about 0.01% to 15.0%, preferably about 0.10% to 10.0%, water-soluble calcium salt; (ii) from about 0.01% to 15.0%, preferably about 0.10% to 10.0% water-soluble phosphate salt, optionally from about 0.0001% to 0.5% and preferably from about 0.0002% to 0.01% water-soluble fluoride salt, (iii) wherein there is an encapsulating coating on at least one of the water-soluble salts that either readily dissolves, disposes or emulsifies in saliva, (iv) from about 10.0% to 95.0% of a gum base; and (v) wherein when the salts are contacted with saliva the pH is between about 4.0 and 7.0 and preferably between about 5.0 and 5.75.

While applicants do not wish the scope of the present invention to be limited by theory, it is believed that the calcium, phosphate, and fluoride ions diffuse through the tooth surface to the demineralized subsurface and precipitate in the demineralized subsurface where they remineralize the tooth structure. This is surprising because sufficient calcium, phosphate, and fluoride ions remain soluble for a period of time sufficient to permit their diffusion into the demineralized subsurface of the dental enamel.

Chemically equivalent concentrations are not necessary as long as the molar ratio of calcium and phosphate ions in the mixture is from about 0.01 to up to 100 to 1. It is preferred that the ratio is from about 0.2 to 1 up to 5 to 1, and it is most preferred that the ratio is between about 1 to 1 and 1.67 to 1; the ratio of calcium to phosphate in unsoluble calcium phosphate salts.

With regard to the length of time of exposure to the teeth of the solutions formed in the oral cavity it is necessary that the period of time be great enough to allow diffusion of the ions into the demineralized subsurface. At least about one minute is required for the release of the salts from the gum and for diffusion. The chewing gum is preferably masticated with the teeth for from about 5 minutes to about 15 minutes or more. The pH of the solution remains relatively constant after its introduction into the oral cavity. Calcium phosphate may precipitate at this pH, but most surprisingly, while some of the precipitation may occur immediately sufficient calcium, phosphate and fluoride ions remain in solution to diffuse into the teeth and remineralize the demineralized dental enamel. It is believed that the ability of the solutions to provide ions for remineralization is greatest upon their first introduction into the oral cavity, thereafter decreasing.

With a chewing gum and the like, mixing is achieved on the surface to the teeth while chewing. The essence of the present invention lies with the stable, single part product and in the mixing and dissolution of the product components when the gum is chewed in the mouth, resulting in an aqueous solution which will precipitate calcium phosphate, calcium fluoride, or calcium fluoro-apatite in the subsurface enamel of the teeth. Surprisingly, the solution can have a pH of about 4.0 to 7.0, but preferably about 5.0 to 5.75 to achieve this result. At a pH below about 3, demineralization occurs rapidly. A pH below 2.5 is generally undesirable from a safety standpoint.

The pH of the saliva solutions in the oral cavity may be adjusted to the pH desired by methods well known in the art. The pH may be controlled by the addition of any acid which is safe for use in the oral cavity and which yields the desired pH at the amount employed. Examples of suitable acids are acetic acid, phosphoric acid, hydrochloric acid, citric acid and malic acid; by the addition of a base, for example, sodium hydroxide; or buffered, for example with sodium citrate benzoate, carbonate, or bicarbonate, disodium hydrogen phosphate, sodium dihydrogen phosphate, etc. Preferably the remineralizing salts employed can be selected to obtain the desired pH. Usually a combination of monobasic, dibasic and/or tribasic alkali metal phosphate salt is selected to provide the target pH.

Pursuant to the present invention, the remineralizing compositions are incorporated into chewing gum. The chewing gum may be any of a variety of different chewing gums, bubble gums, dragees, and the like, including low or high moisture, sugar or sugarless, wax-containing or wax-free, low calorie (via high base or low calorie bulking agents), and/or may contain other dental health agents.

Chewing gum generally consists of a water insoluble gum base, a water soluble portion, and flavors. The water soluble portion dissipates with a portion of the flavor over a period of time during chewing. The gum base portion is retained in the mouth throughout the chew.

The insoluble gum base generally comprises elastomers, resins, fats and oils, softeners, and inorganic fillers. The gum base may or may not include wax. The insoluble gum base can constitute about 5% to 95%, by weight, of the chewing gum, more commonly, the gum base comprises about 10% to 50% of the gum, and in some preferred embodiments, about 20% to 35%, by weight, of the chewing gum.

In an embodiment, the chewing gum base of the present invention contains about 20% to 60% synthetic elastomer, 0 to about 30% natural elastomer, about 5% to 55% elastomer plasticizer, about 4% to 35% filler, about 5% to 35% softener, and optional minor amounts (about one percent or less) of miscellaneous ingredients such as colorants, antioxidants, etc.

Synthetic elastomers may include, but are not limited to, polyisobutylene with GPC weight average molecular weight of about 10,000 to 95,000, isobutylene-isoprene copolymer (butyl elastomer) styrene-butadiene copolymers having styrene-butadiene ratios of about 1 to 3 up to 3 to 1, polyvinyl acetate having GPC weight average molecular weight of about 2,000 to about 90,000, polyisoprene, polyethylene, vinyl acetate-vinyl laurate copolymer having vinyl laurate content of about 5% to 50% of the copolymer, and combinations thereof.

Preferred ranges are, for polyisobutylene, 50,000 to 80,000 GPC weight average molecular weight, for styrene-butadiene, 1 to 1 up to 1 to 3 bound styrene-butadiene, for polyvinyl acetate, 10,000 to 65,000 GPC weight average molecular weight with the higher molecular weight polyvinyl acetates typically used in bubble gum base, and for vinyl acetate-vinyl laurate, vinyl laurate content of about 10% to 45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters of partially hydrogenated rosin, glycerol esters polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithtn, mono-, di- and triglycerides, acetylated monoglycerides, fatty acids (e.g., stearic, palmitic, oleic and linoleic acids), and combinations thereof.

Colorants and whiteners may include FD&C-type dyes and lakes, fruit and vegetable extracts, titanium dioxide, and combinations thereof.

The base may or may not include wax.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately about 0.5% to 15% by weight of the chewing gum. The softeners may include glycerin, lecithtn, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components, bulk sweeteners typically constitute 5 to about 95% by weight of the chewing gum, more typically, 20 to 80% by weight, and more commonly, 30 to 60% by weight of the gum.

Sugar sweeteners generally include saccharide-containing components commonly known in the chewing gum art, including, but not limited to, sucrose, dextrose, maltose, dextrin, dried invert sugar, fructose, levulose, galactose, corn syrup solids, and the like, alone or in combination.

Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination with the above, Preferred sweeteners include, but are not limited to sucralose, aspartame, salts of acesulfame, alitame, saccharin and its salts, cyclamic acid and its salts, glycyrrhizin, dihydrochalccones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Usage level of the artificial sweetener will vary greatly and will depend on such factors as potency of the sweetener, rate of release, desired sweetness of the product, level and type of flavor used and cost considerations. Thus, the active level of artificial sweetener may vary from about 0.02% to 8.0%. When carriers used for encapsulation are included, the usage level of the encapsulated sweetener will be proportionately higher.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Example of low caloric bulking agents include: polydextrose; Raftilose, Raftilin; Fructooligosaccharides (NutraFlora); Palatinose oligosaccharide; Guar Gum Hydrolysate (Sun Fiber); or indigestible dextrin (Fibersol). However, other low calorie bulking agents can be used.

A variety of flavoring agents can be used. The flavor can be used in amounts of about 0.1% to 15.0% of the gum, and preferably, about 0.2% to 5.0%. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

The chewing gum may either be sugarless or sugar containing. However, in an embodiment of the present invention, the chewing gum is sugar containing. This also overcomes some of the sensory quality problems of sugarless gums, Still further, such a chewing gum overcomes some of the other problems of sugarless gum. For example, some sugarless gums may be poorly tolerated by some chewers, who manifest gastrointestinal disturbances, because of the sugar alcohols used in sugarless gums.

Another component which is optionally used in the present invention is a dental abrasive dental abrasives are particularly valuable in chewing gums due to the polishing action which occurs during mastication. The term dental abrasive includes all manner and form of such materials which are normally used in toothpaste, chewing gums, and the like. Specifically dicalcium diphosphate dihydrate is the preferred dental abrasive of the present invention. This particular material also serves to function as an alkaline buffer as described above.

Further dental abrasives which may be utilized in the present invention include calcium carbonate, sodium metaphosphate, aluminum hydroxide, magnesium carbonate, calcium sulphate, silicas including aerogels and xerogels, and tricalcium phosphate. The amount of the dental abrasive employed in the present invention is generally within the range of from about 1.0% to 30.0%, preferably from about 1.5% to about 20.0% by weight.

Yet another optional ingredient in the present invention is the use of glycerine. In the chewing gum aspect of the present invention glycerine serves to soften and maintain the chewability of the chewing gum for prolonged periods. The glycerine also adds to the sweetness of the composition. The glycerine is ordinarily added at levels of from about 0.01% to 10.0%, preferably at from about 0.2% to 5.0% by weight of the composition.

The present invention includes as additional optional components water or a monohydric alcohol at from about 2.0% to 99.0%, preferably at from about 5.0% to 70.0%, and most preferably from about 10.0% to 50.0% by weight of the composition. It is of course recognized that it is particularly valuable to use mixtures of water and the monohydric alcohol generally within the weight ratio of from about 20 to 1 up to 1 to 20, preferably from about 10 to 1 up to 1 to 10.

The preferred monohydric alcohols are methanol, ethanol, or isopropanol although other monohydric alcohols generally including those having up to 18 carbon atoms may be utilized in the present invention. The preferred monohydric alcohol is ethanol. It should be recognized that where the product will be ingested that only ethanol should be used.

product to 2 parts saliva and mixed together immediately before immersion of the enamel specimens.

The two part oral remineralizing treatment was prepared as follows:

|  | Control A | | Example 1 | | Example 2 | | Example 3 | |
| --- | --- | --- | --- | --- | --- | --- | --- | --- |
|  | Part A | Part B | Part A | Part B | Part A | Part B | Part A | Part B |
| Calcium nitrate | 3.00 | 0.00 | 3.0 | 0.00 | 3.0 | 0.00 | 3.00 | 0.00 |
| Magnesium chloride | 0.00 | 0.00 | 0.4 | 0.00 | 0.8 | 0.00 | 0.8 | 0.00 |
| Monopotassium phosphate | 0.00 | 2.00 | 0.0 | 2.10 | 0.0 | 2.10 | 0.0 | 2.40 |
| Dipotassium phosphate | 0.00 | 0.70 | 0.0 | 0.60 | 0.0 | 0.60 | 0.2 | 0.20 |
| Sodium fluoride | 0.00 | 0.50 | 0.0 | 0.50 | 0.0 | 0.50 | 0.0 | 0.00 |
| Sodium MFP | 0.00 | 0.00 | 0.0 | 0.00 | 0.0 | 0.00 | 0.0 | 1.80 |
| Glycerine | 24.00 | 22.85 | 24.0 | 22.85 | 24.0 | 22.85 | 24.0 | 22.85 |
| Water | 73.00 | 73.95 | 72.6 | 73.95 | 72.2 | 73.95 | 72.2 | 72.75 |

The pH of each after mixing the two parts was approximately 5.5.

|  | Crest | Control A | Example 1 | Example 2 | Example 3 |
| --- | --- | --- | --- | --- | --- |
| Hardness increase | 16 | 20.0 | 62 | 49.0 | 21.0 |

A typical process for preparing the chewing gum compositions is as follows. The gum base is melted (about 85° C. to about 90° C.), cooled to 78° C. and placed in a pre-warmed (60° C.) standard mixing kettle equipped with sigma blades. The emulsifier is then added. Next, a portion of the sorbitol and the glycerin is added and mixed for an additional 3 to 6 minutes. The mixing kettle is cooled and mannitol and the remainder of the sorbitol and glycerin are then added and mixing is continued. At the time, the unflavored chewing gum temperature is about 39° C. to 42° C. Flavor oil is then added and incorporated into the base and the mixing is continued. Finally, the sweetener material is added and mixed for an additional 1 to 10 minutes. The remineralization system is added as the last ingredient. The final gum temperature is about 39° C. to 43° C. The chewing gum composition is then discharged from the kettle, rolled, scored and formed into chewing gum pieces.

The following examples serve to provide further appreciation of the invention but are not meant in any way to restrict the effective scope of the invention. All percentages throughout the specification are by weight % unless otherwise indicated.

EXAMPLES 1-3

The following Examples 1-3 and Example 4 describe protocol utilized to evaluate remineralizing products and illustrate their efficacy.

Artificial lesions, about 50 u deep, were formed in one surface of bovine enamel chips using a demineralizing Carbopol gel, which was used to treat the specimens for 72 hours. The surface hardness of the surface to be treated was then measured.

The regimen cycle consisted of a 30 minute demineralization in a standard demineralizing solution followed by a 5 minute treatment of the test products diluted 1 part product to two parts human saliva, followed by a 60 minute remineraltzation in human saliva. Overnight, which was every fifth cycle, the specimens were kept with a layer of saliva and stored in a cold room. The test ran for three days, from a total of 15 demineralization:treatment:remineralization cycles.

For the treatment cycle, the two parts of the remineralizing test agents of the example were separately diluted 1 part The results show that Examples 1 and 2 containing sodium fluoride and magnesium chloride significantly outperform Control A and Crest which do not contain magnesium chloride. Example 3 containing sodium monofluorophosphate and magnesium chloride performed equal to Control A and better than Crest. This is surprising since sodium monofluorophosphate is generally less effective at promoting remineralization than sodium fluoride.

EXAMPLE 4

The following formulations were prepared:

|  | Example 4 | | Control B* | |
| --- | --- | --- | --- | --- |
|  | Part A | Part B | Part A | Part B |
| Calcium nitrate | 3.0 | 0.0 | 0.0 | 0.0 |
| Magnesium chloride | 0.8 | 0.0 | 0.0 | 0.0 |
| Monopotassium phosphate | 0.0 | 0.6 | 0.0 | 0.0 |
| Dipotassium phosphate | 0.0 | 2.1 | 0.0 | 0.0 |
| Glycerine | 24.0 | 22.85 | 50.0 | 50.0 |
| Water | 72.2 | 74.45 | 50.0 | 50.0 |

*The pH of the control was adjusted to 5.5.

A similar treatment regimen was performed as for Examples 1-3 except that in Test 1 the treatment time was 15 minutes using the formulation of Example 4. In Test II, and Control Test III the first cycle of the way was a 5 minute treatment with Crest and cycles 2, 3, 4, and 5 were a 15 minute treatment with the formulation of Example 4 or Control B respectively. The 15 minute treatment time was chosen to replicate what might happen if this formulation was released from a produce where the treatment time might be extended to 15 minutes. The three tests were also compared with a standard Crest treatment in which Crest treatment was applied 5 times per day for 5 minutes. The test was run for 3 days for a total of 15 cycles.

|  | Test I<br>Example 4<br>5 cycles/<br>day | Test II<br>Example 4<br>4 cycles/<br>day<br>Crest<br>1 cycle/<br>day | Control<br>Test III<br>Control B<br>4 cycles/<br>day<br>Crest<br>1 cycle/<br>day | Crest<br>5 cycles/<br>day |
|---|---|---|---|---|
| Hardness increase | 10.0 | 13 | 6.0 | 16 |

The results show that treatments with the non-fluoride containing remineralizing formulation was effective in remineralizing teeth. Test 1 illustrates it was slightly less effective on a one to one treatment basis with Crest. However, Test II compared to Control Test III illustrates it was more effective than Crest on a five to one treatment basis than Crest. When used with the fluoride toothpaste the remineralizing treatments had an additive remineralizing effect. This demonstrates the likely positive effects of a non-fluoride product, i.e., a lozenge or candy containing the remineralizing ingredients if repeated several times a day e.g. after eating.

EXAMPLES 5-7

Examples 5-7 illustrate various embodiments of the present invention. Examples 5-7 represent both sugarless (Examples 5-6) and chewing gum containing sugar (Example 7). All contain divalent metal salts as stabilizers.

|  | Examples | | |
|---|---|---|---|
|  | 5 | 6 | 7 |
| Calcium lactate | 7.0 | — | 1.5 |
| Calcium acetate | — | 4.0 | 3.5 |
| Monopotassium phosphate | 2.8 | 3.3 | 4.0 |
| Dipotassium phosphate | 0.3 | 0.2 | 0.4 |
| Magnesium oxide | 0.2 | 0.3 | 0.3 |
| Gum Base | 25.0 | 30.0 | 20.0 |
| Sugar | — | — | 58.5 |
| Glucose | — | — | 10.0 |
| Sorbitol Powder | 34.6 | 54.85 | — |
| Mannitol Powder | 15.0 | — | — |
| Maltitol Powder | 10.0 | — | — |
| Flavor | 1.5 | 1.3 | 1.8 |
| Glycerine | 3.5 | 6.0 | — |
| Saccharin | 0.1 | — | — |
| Aspartame | — | 0.05 | — |

EXAMPLES 8-10

Examples 8-10 illustrate further embodiments of the present invention.

Example 8 illustrates an embodiment where the calcium salt is encapsulated with a hydrophilic polymer; no divalent metal salt stabilizer is employed.

Example 9 illustrates an embodiment where the calcium salt is encapsulated with a hydrophobic polymer; a divalent metal salt stabilizer is employed.

Example 10 illustrates an embodiment where a dessicant is employed in the anhydrous chewing gum product; no encapsulation or divalent metal salts are employed.

|  | Examples | | |
|---|---|---|---|
|  | 8 | 9 | 10 |
| Calcium lactate<br>(Hydrophilic polymer encapsulated) | 7.0 | — | — |
| Calcium acetate | — | — | 5.0 |
| Calcium acetate<br>(Hydrophobic polymer encapsulated) | — | 4.0 | — |
| Monopotassium phosphate | 2.8 | 3.3 | 4.0 |
| Dipotassium phosphate | 0.3 | 0.2 | 0.4 |
| Magnesium oxide | — | 0.3 | — |
| Anhydrous magnesium chloride (dessicant) | — | — | 1.0 |
| Gum Base | 25.0 | 30.00 | 20.0 |
| Sugar | — | — | 57.8 |
| Glucose | — | — | 10.0 |
| Sorbitol (solution 70%) | — | 15.0 | — |
| Sorbitol Powder | 34.8 | 39.85 | — |
| Mannitol Powder | 15.0 | — | — |
| Maltitol Powder | 10.0 | — | — |
| Flavor | 1.5 | 1.3 | 1.8 |
| Glycerine | 3.5 | 6.0 | — |
| Saccharin | 0.1 | — | — |
| Aspartame | — | 0.05 | — |

EXAMPLES 11-12

An additional study was performed using the formulations below in order to illustrate remineralization hardness:

|  | EXAMPLE 11 | EXAMPLE 12 |
|---|---|---|
| Calcium nitrate | 4.6 | 6.7 |
| Magnesium chloride | 0.8 | — |
| Stannous chloride | — | 0.04 |
| Water | 94.6 | 93.26 |
| Dipotassium phosphate | 0.38 | 0.5 |
| Monopotassium phosphate | 2.32 | 3.4 |
| Water | 97.3 | 96.1 |

The regimen for this test was similar to the previous tests of Examples 1-4. However, half of each chip was covered with tape to serve as an untreated control.

Hardness results are shown below:

| Example 11 | Example 12 |
|---|---|
| 5.7 | 7.8 |

Three of the specimens from Example 11 and four specimens from Example 12 were sliced across the tape to expose both the treated and untreated portions of the lesion. SEM photomicrographs of each specimen were then prepared.

Examination of the SEMs clearly shows the presence of remineralization in 6 of the seven specimens examined as shown by a reduction in the holes and fissures in the treated sides of the specimens.

What is claimed is:

1. A chewing gum product for remineralizing at least one subsurface lesion and/or mineralizing at least one exposed dentinal tubule in at least one tooth, comprising:
   (i) a water-soluble cationic portion comprising from about 0.01% to 15.0% of at least one water-soluble calcium salt;
   (ii) a water-soluble anionic portion comprising from about 0.01% to 15.0% of at least one water-soluble phosphate salt;
   (iii) from about 10.0% to 95.0% of a gum base; and (iv) at least one encapsulating coating disposed on one or both of said cationic and anionic portions, wherein said encapsulating coating is present in an amount and is comprised of a material such that (a) said encapsulating coating substantially inhibits reaction of said cationic and anionic portions during storage of said product, and (b) when said product is chewed and contacted with saliva, said encapsulating coating releases said encapsulated cationic and/or anionic portion at a rate such that said cationic and anionic portions of said product are simultaneously released into said saliva, thereby forming a mixed aqueous solution which comprises cations released by said cationic portion and anions released by said anionic portion and further which simultaneously delivers said cations and anions to a surface of said tooth, said cationic and anionic portions each having a pH in water such that said mixed aqueous solution has a pH of from about 4.0 to 7.0.

2. The chewing gum product according to claim 1, wherein said cationic and anionic portions are each coated with said at least one encapsulating coating, further wherein said encapsulating coating disposed on said cationic portion and said encapsulating coating disposed on said anionic portion constitute identical materials.

3. The chewing gum product according to claim 2, wherein said encapsulating coating disposed on said cationic portion and said encapsulating coating disposed on said anionic portion constitute identical materials having substantially identical thicknesses.

4. The chewing gum product according to claim 1, wherein said at least one encapsulating coating has a thickness of from about 0.1 to 20 microns.

5. The chewing gum product of claim 1, wherein said at least one encapsulating coating comprises a material selected from the group consisting of oleophilic materials, edible materials, polymeric materials, resin materials, waxes and mineral oils.

6. The chewing gum product according to claim 5, wherein said at least one encapsulating coating is a polymeric material selected from the group consisting of hydrophilic organic polymers, hydrophobic organic polymers and mixtures thereof.

7. The chewing gum product according to claim 6, wherein said polymeric material is a hydrophilic polymer selected from the group consisting of water-soluble organic polymers and water-dispersible organic polymers.

8. The chewing gum product according to claim 7, wherein said hydrophilic polymer is selected from the group consisting of gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide and polyvinyl alcohol/acetate.

9. The chewing gum product according to claim 7, wherein said hydrophilic polymer is selected from the group consisting of a polyethylene glycol having a molecular weight of 4000, a polyvinylpyrrolidone, a polyethylene oxide having a molecular weight of 4,000,000, and a partially hydrolyzed polyvinyl acetate.

10. The chewing gum product according to claim 6, wherein said polymeric material is a hydrophobic organic polymer selected from the group consisting of polyvinyl acetate, polyacrylamide, polyvinyl chloride, polystyrene, polyethylene, and polyurethane.

11. The chewing gum product according to claim 10, wherein said hydrophobic polymer comprises from about 5.0% to 30.0% by weight of a particulate water-extractable organic or inorganic filler.

12. The chewing gum product according to claim 5, wherein said at least one encapsulating coating comprises a polymeric material which is applied to said anionic and/or cationic portion by a process selected from the group consisting of pan coating, fluidized coating and centrifugal fluidized coating.

13. The chewing gum product according to claim 5, wherein said at least one encapsulating coating comprises a polymeric material which is applied to said anionic and/or cationic portion in the form of an emulsion or suspension, wherein after application to said cationic and anionic portions, said emulsion or suspension undergoes evaporation so as to remove a solvent medium thereof to form a continuous film coating which encapsulates said cationic and anionic portions.

14. The chewing gum product according to claim 5, wherein said at least one encapsulating coating comprises a polymeric material which constitutes from about 5.0 to about 50.0 percent of the combined dry weight of the coated cationic and anionic portions.

15. The chewing gum product according to claim 5, wherein said at least one encapsulating coating is an oleophilic material selected from the group consisting of paraffin, mineral oil, edible oils, organic esters and edible polysiloxanes.

16. The chewing gum product according to claim 15, wherein said oleophilic material is an edible oil selected from the group consisting of peanut oil, coconut oil, palm oil, and safflower oil.

17. The chewing gum product according to claim 15, wherein said oleophilic material is an organic ester selected from the group consisting of isopropyl siloxane myristate, and isopropyl palmitate.

18. The chewing gum product according to claim 5, wherein said at least one encapsulating coating comprises an edible gum.

19. The chewing gum product according to claim 1 wherein the chewing gum product contains from about 0.0001% to 0.5% of at least one water-soluble fluoride salt which yields fluoride ions.

20. The chewing gum product according to claim 1 wherein the encapsulating coating comprises between about 5.0% to 50.0% of the surface-coated calcium, phosphate, or fluoride salt particle dry weight.

21. The chewing gum product according to claim 1 wherein the encapsulating coating is a hydrophilic polymer or water-insoluble polymer or a mixture thereof.

22. The chewing gum product according to claim 1 wherein the encapsulating surface-coating on the calcium, phosphate, or fluoride salt particles is a hydrophilic polymer having a content between about 5.0% to 95.0% of a water-insoluble polymer, based on the coating weight.

23. The chewing gum product according to claim 1 wherein the encapsulating polymer is a hydrocolloid.

24. The chewing gum product according to claim 1 wherein the encapsulating polymer is polyvinyl acetate.

* * * * *